United States Patent [19]

Hartung et al.

[11] Patent Number: 5,436,007
[45] Date of Patent: Jul. 25, 1995

[54] DIAPER RASH LOTION

[75] Inventors: Donald E. Hartung, Arlington Heights, Ill.; Murray J. Sibley, Westerville, Ohio; Steven J. McConaghy, Westerville, Ohio; Marvin G. Cross, Westerville, Ohio; Rosalyn Ruland, Bexley, Ohio

[73] Assignee: Abbott Laboratories, Abbott Park, Ill.

[21] Appl. No.: 77,308

[22] Filed: Jun. 15, 1993

Related U.S. Application Data

[63] Continuation-in-part of Ser. No. 965,829, Oct. 23, 1992, abandoned.

[51] Int. Cl.$^6$ .......................... A61K 9/10; A61K 47/34
[52] U.S. Cl. .................................... 424/402; 514/856; 514/772.3
[58] Field of Search ................ 424/402; 514/846, 865, 514/941; 523/122

[56] References Cited

U.S. PATENT DOCUMENTS

| | | | |
|---|---|---|---|
| 4,556,560 | 12/1985 | Buckingham | 514/865 |
| 4,854,333 | 8/1989 | Inman et al. | 424/70 |
| 4,904,524 | 2/1990 | Yoh | 428/311.3 |
| 4,996,238 | 2/1991 | Matravers | 514/865 |

FOREIGN PATENT DOCUMENTS 1357731 6/1974 United Kingdom .
WO92/09289 6/1992 WIPO .

OTHER PUBLICATIONS

"A Buffered Cream for Napkin Rashes", *The Practitioner*, 210:824–828 (1973).

*Primary Examiner*—Edward J. Webman
*Attorney, Agent, or Firm*—Lonnie R. Drayer; Donald O. Nickey

[57] ABSTRACT

A skin lotion containing a linear polydimethylsiloxane polymer, a non-ionic emulsifier, consisting of polyoxyethylene sorbitan fatty acid esters, sorbitan fatty acid esters, polyoxyethylene alcohols, or polyoxyethylene fatty ethers aloe vera, an alkoxylated ether/ester, sodium citrate, citric acid, a blend of propylene glycol, diazolidinyl urea, methyl paraben and propyl paraben, and water. Most preferably the buffering system results in the lotion having a pH of about 5.2 which neutralizes acidic and basic by-products of urine and fecal matter. The lotion has a preferred viscosity in the range of 10–20,000 centipoise. The lotion is easily washed off with soap and water and is useful in the protection and treatment of diaper rash.

13 Claims, No Drawings

DIAPER RASH LOTION

This application is a continuation-in-part of application U.S. Ser. No. 07/965,829, filed on Oct. 23, 1992, now abandoned

TECHNICAL FIELD

The present invention relates generally to a skin lotion for use in connection with diaper rash.

BACKGROUND ART

One of the most common skin problems with infants relates to diaper rash, also known as diaper dermatitis. One study conducted with infants less than two years of age concluded that almost two-thirds of all infants suffer from diaper rash of some degree. Approximately 10% of all infants can have their diaper rash classified as being moderate, with another 5% of the infants having diaper rash which could be classified as severe.

The primary contributors to the development of diaper rash have long been thought to be infant urine and feces. For example, infants under two months of age can urinate up to 20 times per day. Thereafter, infants can urinate up to 8 times a day. In addition, infant defecation typically occurs several times a day.

It had been theorized that the breakdown of the urine to yield ammonia primarily contributed to the formation of diaper rash by increasing the alkalinity of the skin. However, more recent studies have concluded that the primary contributor to the development of diaper rash is feces. As opposed to the alkaline pH associated with urine, feces typically exhibits an acidic pH due to bile. In fact, studies have shown that diaper rash is more prominent in the presence of feces than in the presence of urine, thereby providing a plausible explanation for the problems with diaper rash associated with infants who have diarrhea or frequent stools.

Diaper rash may predispose an infant to irritation and infection. The two most common types of infection are those associated with yeast, and bacteria. The most common yeast infection is caused by *Candida albicans*. Meanwhile, the most common bacterial infection is caused by *Staphylococcus aureus*.

Treatment for diaper rash involves removing the source of irritation, reducing the immediate skin reaction, relieving the discomfort and preventing secondary infection and other complications. Frequent diaper changes and keeping the area as dry and clean as possible normally prove helpful. However, merely keeping the area clean and dry does not protect the irritated skin from the chemical irritation associated with the by-products of infant urine and feces.

In response to the problems associated with diaper rash, a number of products have been made available. The principle function of these products has been to act as a protectant, such that any affected area is protected against further direct contact with urine or feces. The most widely used protective ingredient has been zinc oxide. While many preparations contain zinc oxide in concentrations of approximately 10% by weight, some of the more popular brands have zinc oxide concentrations of approximately 40% by weight. Unless otherwise stated, the percentage concentrations of ingredients is understood to refer to present by weight. Typically the zinc oxide is formulated with an oily substance such as petrolatum. Consequently, although such a diaper rash compound provides an effective protective layer, it is greasy, messy to apply, and not easily removed from the hands or the baby's bottom. Although removal can be affected with mineral oil, having to wash one's hands with mineral oil is inconvenient. Additionally, zinc oxide products have a distinctive smell due to their oil base, with this smell being offensive to some users of the product.

Most of the diaper rash products currently available are in the form of an ointment or a water-in-oil emulsion. The high viscosity associated with these products keeps the diaper rash product from being washed away by urine or feces. In many cases, the high viscosity is the result of the inclusion of zinc oxide. Thus, the typical anhydrous, hydrophobic ointment prevents urine or feces from coming into direct contact with the skin by their being repelled from the ointment surface. As such, the product acts as a barrier, inhibiting any penetration into the diaper rash product by any liquid.

An example of a diaper rash product is British Patent No. 1,357,731. That patent discloses a unique powder composition, which can be incorporated into a hydrophobic ointment. A buffer system is provided to buffer the composition at a pH of from 5.5 to 7.5, and preferably from 6 to 7. That patent discloses that a citric acid/sodium citrate buffering system does not have superior buffering capacity when compared with other buffering systems. This patent further discloses that "succinic acid/sodium succinate has 30% more buffering capacity than a citric acid/sodium citrate" buffer system. Thus this patent differs from the instant Invention in that it claims use of a powder formulation having buffering capacity in the alkaline range of pH 5.5 to 7.5, and teaches away from the use of citric acid buffering system in view of the aforenoted comments related to the preferred use of a succinic acid buffer.

Another example of the prior art is U.S. Pat. No. 4,556,560 issued on Dec. 3, 1985 to Buckingham. This patent discloses and claims use of lipase inhibiting agents, such as the water soluble metallic salts including zinc chloride, in the treatment of diaper rash. This patent purports to treat diaper rash by inhibiting the deleterious effects of the enzyme lipase action on the skin, said inhibition being achieved by incorporating a inhibitory agent of said lipase action into a barrier like carrier, said carrier having the characteristics of being relatively hydrophobic in nature thereby forming an effective barrier to the skin against urine and feces. The instant Invention does not disclose nor claim use of lipase inhibitory agents. The instant Invention is further distinguished from the Buckingham patent in that the present invention specifically claims use of a buffering sysytem to neutralize acidic conditions. Buckingham neither teaches nor claims any buffering system. Further the instant Invention is see apart from the Buckingham patent in the nature of the carrier material employed in the formation of the so-called skin barrier. In the case of Buckingham, specifically disclosed are water-in-oil types of emulsions. In contrast to Buckingham, the instant Invention specifically discloses and claims use of oil-in-water type emulsions in the formation of the barrier material.

Yet another example of the prior art is U.S. Pat. No. 4,996,238 issued on Feb. 26, 1991 to Matravers. This patent discloses and claims a skin protective composition exhibiting enhanced water repellency and skin conditioning effects and contains aliphatic waxes and hydrophobic silicones. Matravers' specificically discloses and claims the use of an admixture consisting of a fatty acid admixed with one or more hydrophobic silicones. This composition is devoid of water and further no buffering system is claimed. In contrast, the instant Invention claims a water-based liquid product which contains a buffering system effective in acidic conditions.

Another example of the prior art is U.S. Pat. No. 4,904,524 issued on Feb. 27, 1990 to Yoh. This patent discloses and claims the encapsulation and microbead formation and use thereof of the active silicon agent (Dimethicone) in the preparation of cloth wipes in the treatment of diaper rash. This patent specifically discloses the need for an elevated concentration of encapsulated beads containing the active agent at the surface of the wipe. The stability, presence and delivery of the active agent within the wipe is directly linked to, and dependent on the process used to form and adhere the encapsulated beads to the paper wipe. In contrast, the instant Invention claims a water-based liquid product which contains a buffering system effective in acidic conditions. Further, the instant Invention does not require, teach nor claim encapsulation of Dimethicone, one of the ingredients in the claimed composition.

Other studies, such as one published in *The Practitioner*, Vol 210:824–828 (1973), discuss a boric acid/borax buffer system for use as a diaper rash product. However, studies conducted during the 1970's brought about concerns of boron toxicity such that products containing boric acid had to be reformulated thereby eliminating boric acid as an ingredient.

Still another approach to products containing anhydrous, hydrophobic zinc oxide was the incorporation into such products of alkoxylated ether/esters Such as polypropyleneglycol myristyl ether propionate. Although this approach rendered the diaper rash products less greasy, it did not completely resolve the problem associated with the zinc oxide content.

It is thus apparent that a need exists for an improved diaper rash product which provides a safe system, which is easy to apply as well as easy to remove by simple cleaning agents such as soap and water.

DISCLOSURE OF THE INVENTION

There is disclosed a skin cream comprising stearic acid, a linear polydimethylsiloxane polymer, a non-ionic emulsifier composed of a mixture of cetearyl alcohol and its ethoxylate, mineral oil, aloe vera, an alkoxylated ether/ester, sodium citrate, citric acid, a naturally derived, non-ionic, water soluble polymer, a blend of propylene glycol, diazolidinyl urea, methyl paraben, and propyl paraben, and water. Preferably the sodium citrate and citric acid cooperate to form a buffering system having a pH in the range of between 3.5 and 6.5. More preferably the sodium citrate and citric acid cooperate to form a buffering system having a pH in the range of between 4.8 and 5.6. Most preferably the sodium citrate and citric acid cooperate to form a buffering system having a pH of 5.2.

In the skin cream of this invention, the naturally derived, non-ionic water-soluble polymer preferably is nonoxynyl hydroxyethylcellulose. Additionally, the skin cream has a neutral olfactory sensation. The viscosity of the skin cream is in the range of between 50,000 centipoise and 200,000 centipoise. Additionally, the skin cream is soluble in soap and water. Furthermore, the stearic acid has a saponification value of between 197 and 200, and an iodine value of not more than 1. Still further, the mineral oil is a light mineral oil with a specific gravity of between 0.818 and 0.880.

There is also disclosed a skin cream comprising stearic acid having a saponification value of between 197 and 200, and an iodine value of not more than 1, with the stearic acid also of a concentration of about 10% by weight, a linear polydimethylsiloxane polymer of a concentration of about 20% by weight, a non-ionic emulsifier, said emulsifier being of a concentration of about 8% by weight, light mineral oil with a specific gravity of between 0.818 and 0.880 of a concentration of about 4% by weight, aloe vera of a concentration of about 1% by weight, an alkoxylated ether/ester of a concentration of about 5% by weight, sodium citrate of a concentration of about 3% by weight, citric acid of a concentration of about 0.5% by weight, water of a concentration of about 47% by weight, a naturally derived, non-ionic water soluble polymer of a concentration of about 0.5% by weight, and a blend of propylene glycol, diazolidinyl urea, methyl paraben, and propyl paraben, said blend of a concentration of about 1% by weight.

The skin cream is soluble in soap and water and has a viscosity in the range of between 50,000 centipoise and 200,000 centipoise. The sodium citrate and citric acid cooperate to form a buffering system having a pH in the range of between 3.5 and 6.5. The alkoxylated ether/ester is preferably polypropyleneglycol myristyl ether propionate, and said naturally derived, non-ionic water soluble polymer is preferably nonoxynyl hydroxyethylcellulose. More preferably the sodium citrate and citric acid cooperate to form a buffering system having a pH in the range of between 4.8 and 5.6. Most preferably the buffering system has a pH of 5.2.

There is also disclosed a skin cream for use in the prevention and treatment of diaper rash, said skin cream being soluble in soap and water, having a viscosity in the range of between 50,000 centipoise and 200,000 centipoise, and having a buffering system with a pH in the range of 3.5 and 6.5. The buffering system comprises sodium citrate and citric acid. Additionally, the skin cream comprises a linear polydimethylsiloxane polymer. More preferably the buffering system has a pH in the range of between 4.8 and 5.6. Preferably the skin cream comprises a buffering system of a concentration of at least 3.5% by weight. Additionally, the linear polydimethylsiloxane polymer is preferably of a concentration of at least 20% by weight.

There is also disclosed a skin lotion having a viscosity in the range of about 10 to 20,000 centipoise, said lotion comprising a linear polydimethylsiloxane polymer, a non-ionic emulsifier, sodium citrate, citric acid, a blend of propylene glycol, diazolidinyl urea, methyl paraben, and propyl paraben, and water. The sodium citrate and citric acid cooperate to form a buffering system for the lotion having a pH in the range of between 3.5 and 6.5. More preferably the sodium citrate and citric acid cooperate to form a buffering system having a pH in the range of between 4.8 and 5.6. Most preferably the sodium citrate and citric acid cooperate to form a buffering system having a pH of 5.2. The skin lotion preferably has a neutral olfactory sensation.

Additionally, the skin lotion is soluble in soap and water and may also include sodium ethylene diamine tetraacetic acid. Furthermore, the skin lotion preferably includes an alkoxylated ether/ester. Also the skin lotion preferably includes aloe vera.

In a preferred embodiment of the invention the linear polydimethylsiloxane polymer is of a concentration of about 5 to 20% by weight, the emulsifier is of a concentration of about 2 to 6% by weight, the sodium citrate is of a concentration of about 1 to 8% by weight, the citric acid is of a concentration of about 0.1 to 2.0% by weight, the water is of a concentration of about 60 to 90% by weight, and the blend of propylene glycol, diazolidinyl urea, methyl paraben, and propyl paraben is of a concentration of about 1.0% by weight. The skin lotion of this invention is delivered to skin by means of a wipe, a diaper, a spray from an aerosol or pump dispenser, a roll-on or a dabber.

In another preferred embodiment, there is also disclosed a skin lotion comprising a linear polydimethylsiloxane polymer, with linear polydimethylsiloxane polymer of a concentration of about 8 to 12% by weight, a non-ionic emulsifier selected from the group of comprising polyoxyethylene sorbitan fatty acid esters, sorbitan fatty acid esters and poloxyethylene alcohols or polyoxyethylene fatty ethers, with the emulsifier having a concentration of about 3 to 5% by weight, sodium citrate of a concentration of about 2 to 5% by weight, citric acid of a concentration of about 0.3 to 0.9% by weight, water of a concentration of at least 70 to 85% by weight, and a blend of propylene glycol, diazolidinyl urea, methyl paraben, and propyl paraben, with the blend having a concentration of about 1.0% by weight.

The skin lotion disclosed immediately above is soluble in soap and water and preferably has a viscosity of between about 10 to 20,000 centipoise. The viscosity is primarily modified by adding to the composition disodium ethylene diamine tetraacetic acid (herinafter also referred to as sodium EDTA or $Na_2EDTA$) and by changing the concentration of Dimethicone in the range of about 1 to about 30% by weight of the composition. In the presence of low or intermediate concentrations of Dimethicone in the range of about 1 to 15% by weight and in the presence of $Na_2EDTA$ the composition will have a very fluid like character and a viscosity in the range of about 10 to 1,000 centipoise, and more preferably a viscosity of between about 10 to 500 centipoise, and most preferably a viscosity of between about 10 to 100 centipoise. In the presence of relatively high concentrations of Dimethicone in the range of about 15 to 30% and in the absence of sodium EDTA the composition will exhibit a less fluid like character and a viscosity in the range of about 1,000 to 20,000 centipoise, and more preferably a viscosity of between about 8,000 to 18,000 centipoise, and most preferably a viscosity of between about 10,000 to 15,000 centipoise.

In the case of compositions either containing or not containing sodium EDTA, the sodium citrate and citric acid preferably will cooperate to form a buffering system having a pH in the range of between 3.5 and 6.5. More preferably the sodium citrate and citric acid cooperate to form a buffering system having a pH in the range of between 4.5 and 6.0. Most preferably sodium citrate and said citric acid cooperate to form a buffering system having a pH of between 5.0 and 5.5. Buffering capacity is independent of either sodium EDTA or Dimethicone concentrations.

Preferably the skin lotion also includes an alkoxylated ether/ester of a concentration of about 5.0% by weight. More preferably the alkoxylated ether/ester is polypropyleneglycol myristyl ether propionate. Also the skin lotion preferably includes aloe vera of a concentration of about 0 to 5% by weight, more preferably an aloe vera concentration of about 0 to 3% and most preferably an aloe vera concentration of about 0 to 1.5% by weight.

There is also disclosed a skin lotion for use in the prevention and treatment of diaper rash, with this skin lotion being soluble in soap and water, and having a buffering system with a pH in the range of between 3.5 and 6.5, with the buffering system comprising sodium citrate and citric acid. The skin lotion preferably further comprises a linear polydimethylsiloxane polymer, a non-ionic emulsifier, sodium citrate, citric acid, a blend of propylene glycol, diazolidinyl urea, methyl paraben, and propyl paraben, and water.

One aspect of the present invention provides an effective, easy to apply and remove diaper rash lotion having a buffering system to maintain the pH of the product at approximately the natural skin pH.

Another aspect of the present invention provides an effective, easy to apply and remove diaper rash lotion having a buffering system to maintain the pH of the product at approximately the natural skin pH.

Other aspects and advantages of the instant invention will be apparent from the following description, examples, and the appended claims.

DETAILED DESCRIPTION OF THE INVENTION

Specifically, the present invention is concerned with a skin cream or lotion for use primarily in the treatment of diaper rash. The present invention could also be used in an attempt to prevent diaper rash by inhibiting contact with the skin of either feces or urine. The preventative aspect of the product occurs solely due to the protectant included in the formulation of the cream.

Both the diaper rash cream and lotion embodiments of this invention are comprised of an oil-in-water emulsion which incorporates a simple and safe buffering system. More specifically, the buffering system of the present invention is comprised of citric acid and sodium citrate. Although the buffering system is relatively simple, the system's capacity is sufficient to maintain the pH of both the cream and lotion relatively close to the normal pH of skin, despite the addition of significant amounts of either, or both, alkaline and acidic materials, such as ammonia and hydrochloric acid.

Since the cream and lotion embodiments of this invention are an oil-in-water emulsion, the product can be easily removed from the skin or clothing by washing with soap and water. Additionally, the product does not leave a greasy feeling on the skin. Still further, in the preferred embodiment of the invention, no fragrance is added to either the cream, such that the end-product has a neutral olfactory sensation. Importantly the diaper rash cream and lotion of this invention possess excellent protective qualities comparable to those associated with leading diaper rash treatment products, particularly the well known ointments.

In use, the diaper rash cream embodiment of this invention is spread on sufficiently thick over the affected area to allow a good coating of the area to be protected. The infant may then be diapered in either cloth or disposable diapers. When it becomes time to change the baby's diaper, the area can be cleaned, preferably with soap and water, and thereafter allowed to dry before reapplication of the diaper rash cream and re-diapering.

In use, the diaper rash lotion embodiment of this invention is applied over the area to be protected. The infant may then be diapered in either cloth or disposable diapers. When it becomes time to change the baby's diaper, the area can be cleaned, preferably with soap wand water, and thereafter allowed to dry before reapplication of the diaper rash lotion and re-diapering.

BEST MODE FOR CARRYING OUT THE INVENTION

A representative formula for the diaper rash cream of the invention is set forth in Table 1.

TABLE 1

DIAPER RASH CREAM

| INGREDIENT | CONCENTRATION (Percent by weight) |
|---|---|
| Non-ionic emulsifier composed of a mixture of cetearyl alcohol and its ethoxylate | 8% |
| Linear polydimethylsiloxane polymer with an average kinematic viscosity of 100 centistokes | 20% |
| Alkoxylated ether/ester | 5% |
| Light mineral oil with a specific gravity of between 0.818 and 0.880 | 4% |
| Stearic acid with a saponification value between 197–200 and an iodine value of not more than 1 | 10% |
| Aloe vera | 1% |
| A blend of propylene glycol, diazolidinyl urea, methyl paraben and propyl paraben | 1% |
| Sodium citrate | 3% |
| Citric acid | 0.5% |
| Naturally derived, non-ionic, water soluble polymer | 0.5% |
| Purified water | q.s. |

A skin cream according to this invention is prepared in the following manner. Turning to Table 1, the first five listed ingredients are combined and then heated to between 65°–75° C., preferably to between 70°–72° C. The water is then separately heated to between 65°–75° C., and also preferably to between 70°–72° C. As the water is heating the water soluble polymer is added and the resultant solution agitated.

When the temperatures of both liquids are in the desired range, they are combined. Care must be taken that the oil solution not begin to solidify at this time, so it may be easier to add the water solution to the oil solution. Preferably, once the solutions are combined, agitation continues.

The combined solution is then cooled. During cooling, the buffering system is preferably first added. Finally, the aloe and blend of preservatives are added. However, this addition should occur when the temperature of the solution is less than 55° C. The product will begin to thicken once its temperature is between 45°–50° C.

In the preferred cream embodiment of the invention the first component, namely the non-ionic emulsifier is Promulgen D, a blend of a fatty alcohol (cetearyl alcohol) and an ethyoxylated fatty ester (ceteareth-20). Promulgen D is a product distributed by Amerchol Corporation, Edison, N.J., U.S.A. The linear polymer is the protectant associated with this invention. In one embodiment of the invention the protectant is Dow Corning 200 Fluid, 100 cst. This Dimethicone compound is a linear polydimethylsiloxane polymer which is not readily water soluble and has an average kinematic viscosity of 100 centistokes. It will be readily appreciated by those skilled in the art that other larger or smaller polydimethylsiloxane polymers can also be employed in the formulations of the instant Invention.

The alkoxylated ether/ester in the preferred cream and lotion embodiments of the invention is Crodamol PMP, an emollient that cuts down on the greasy feeling associated with Dimethicone. Crodamol PMP is a long chain fatty acid ester comprising polypropyleneglycol myristyl ether propionate. Cromadol PMP is distributed by Croda, Inc. of Parsippany, N.J., U.S.A. The lightweight mineral oil functions as an additional emollient. The stearic acid functions as a thickener. The blend of propylene glycol, diazolidinyl urea, methyl paraben and propyl paraben in the preferred embodiment of the invention is Germaben IIE, a preservative system. Germaben IIE is distributed by Sutton Laboratories of Chatham, N.J. U.S.A. Finally, the naturally derived water soluble polymer in the preferred embodiment of the invention is Amercell HM-1500 a thickener comprising nonoxynyl hydroxyethylcellulose. Amercell 1500 is distributed by Amerchol Corporation of Edison, N.J., U.S.A. Hydroxypropylmethylcellulose could also be utilized as a thickener in place of nonoxynyl hydroxyethylcellulose, however, the Amercell HM-1500 is a more effective thickener in the cream of this invention than is hydroxypropylmethylcellulose.

A representative range of the formula composition for the diaper rash lotion embodiment of the invention is set forth in Table 2. As noted previously the viscosity of this composition can be readily modified through the omission of sodium EDTA in the formulation and by varying the concentrations of Dimethicone.

TABLE 2

Diaper Rash Lotion

| INGREDIENT | CONCENTRATION RANGE (weight %) | | |
|---|---|---|---|
| | Acceptable | Preferred | Most Preferred |
| Non-ionic emulsifier** | 1–10 | 2–6 | 3–5 |
| Dimethicone | 1–30 | 5–20 | 8–12 |
| Sodium citrate | 1–10 | 1–8 | 2–5 |
| Citric acid | 0.17–1.7 | 0.17–1.3 | 0.33–0.83 |
| Aloe Vera Gel | 0–5 | 0–3 | 0–1.5 |
| Preservative | 0.2–3 | 0.2–2 | 0.5–1.5 |
| Disodium EDTA | 0–1 | 0–0.5 | 0–0.3 |
| Purified water | 50–95 | 60–90 | 70–85 |

**Selected from the group of non-ionic emulsifiers comprising polyoxyethylene sorbitan fatty acid esters, sorbitan fatty acid esters, poloxyethylene alcohols and poloxyethylene fatty ethers.

The composition noted in Table 2 has an acceptable viscosity and pH range of about 10 to 20,000 centipoise and about 3.5 to 6.5 respectively. Compositions having a Dimethicone concentration in the range of about 1 to 15% by weight and including sodium EDTA will have an acceptable viscosity and pH range of about 10 to 1,000 centipoise and about 3.5 to 6.5 respectively, a preferred viscosity and pH range of about 10 to 500 centipoise and about 4.5 to 6.0 respectively, and a most preferred viscosity and pH range of about 10 to 100 centipoise and about 5.0 to 5.5 respectively. Compositions having a Dimethicone concentration in the range of about 15 to 30% by weight and not including sodium EDTA will have an acceptable viscosity and pH range of about 1,000 to 20,000 centipoise and about 3.5 to 6.5 respectively, a preferred viscosity and pH range of about 8,000 to 18,000 centipoise and about 4.5 to 6.0 respectively, and a most preferred viscosity and pH range of about 10,000 to 15,000 centipoise and about 5.0 to 5.5 respectively.

A representative specific formula composition for the diaper rash lotion embodiment of the invention having a low viscosity is set forth in Table 3.

TABLE 3

Diaper Rash Lotion: Low Viscosity Product

| INGREDIENT | CONCENTRATION RANGE (weight %) |
|---|---|
| Non-ionic emulsifier** | 4.0 |
| Dimethicone | 10.0 |
| Sodium citrate | 3.0 |
| Citric acid | 0.5 |
| Aloe Vera Gel | 1.0 |
| Preservative | 1.0 |
| Disodium EDTA | 0.2 |
| Crodamol PMP | None |
| Purified water | 80.3 |

**Selected from the group of non-ionic emulsifiers comprising polyoxyethylene sorbitan fatty acid esters, sorbitan fatty acid esters, poloxyethylene alcohols and poloxyethylene fatty ethers.

A representative specific formula composition for the diaper rash lotion embodiment of the invention having a high viscosity is set forth in Table 4.

TABLE 4

Diaper Rash Lotion: High Viscosity Product

| INGREDIENT | CONCENTRATION RANGE (weight %) |
|---|---|
| Non-ionic emulsifier** | 4.0 |
| Dimethicone | 20.0 |
| Stearic Acid | 1.0 |
| Sodium citrate | 3.0 |
| Citric acid | 0.5 |
| Aloe Vera Gel | 1.0 |
| Preservative | 1.0 |
| Disodium EDTA | None |
| Cromadol PMP | 2.0 |
| Purified water | 67.5 |

**Selected from the group of non-ionic emulsifiers comprising polyoxyethylene sorbitan fatty acid esters, sorbitan fatty acid esters, poloxyethylene alcohols and poloxyethylene fatty ethers.

The expected method of preparation for either the low or high viscosity diaper rash lotion formulation was to add the sodium citrate and the citric acid to the water and heat the solution to between 70°-75° C. The oil phase was then added at the same temperature and the product was agitated. Unexpectedly, no emulsification appeared to have occurred. Once agitation was stopped, the product separated into two distinct layers.

Thus, it was discovered that for an emulsified lotion to be formed, the oil phase had to be added to the water, with both liquids at between 70°-75° C. Emulsification took place and cooling was started. At 50° C. the blend of propylene glycol, diazolidinyl urea, methyl paraben and propyl paraben was added. At 43° C. the citric acid was added. At 38° C. the sodium citrate was added. At 30° C. the agitation was stopped. The appearance of the product was good. Additionally, the pH was 5.5 and a viscosity of 750 centipoise was determined. Separation was not noticed at room temperature for four weeks, but upon shaking of the container the two layers were easily combined.

In the preferred skin lotion embodiment of the invention the linear polymer is the protectant associated with this invention. In a preferred embodiment of the invention the linear polydimethylsiloxane polymer protectant employed is Dow Corning 200 Fluid, 100 cst. This Dimethicone compound is not readily water soluble and has an average kinematic viscosity of 100 centistokes. (It will be readily appreciated by those skilled in the art that other larger or smaller linear polydimethylsiloxane polymers could also be used). The blend of propylene glycol, diazolidinyl urea, methyl paraben and propyl paraben in the preferred embodiment of the invention is Germaben IIE, a preservative system.

Two modified lotion embodiments would include either 5% alkoxylated ether/ester or 5% alkoxylated ether/ester and 1% aloe vera. The alkoxylated ether/ester in the modified lotion embodiments of the invention is Crodamol PMP, an emollient that cuts down on the greasy feeling associated with Dimethicone.

Crodamol PMP is a long chain fatty acid ester comprising polypropyleneglycol myristyl ether propionate. In either embodiment, the amount of water is reduced accordingly.

The resultant lotion embodiment is stable and has a viscosity in the range of between 10-20,000 centipoise. The exact viscosity will be determined by the presence or absence of sodium EDTA and stearic acid and the concentration of Dimethicone in the composition.

Preferably the pH for both the lotion and cream is between is between 3.5 and 6.5. More preferably the pH of both the lotion and cream is between 4.8 and 5.6, and most preferably the pH is 5.2.

The invention will be better understood in view of the following examples, which are illustrative only and should not be construed as limiting the invention.

EXPERIMENTAL—DETERMINATION OF CREAM COMPOSITION

EXAMPLE 1—CONTROL

The ingredients in Table 1 were combined, except that neither sodium citrate nor citric acid were added. The resultant cream is easy to apply and remove, however, when subjected to extremes in pH, tends to become more ammoniacal if a base is added, but if a strong acid is added then it tends to become very acidic.

EXAMPLE 2—CONTROL

The ingredients of Table 1 were combined, except that boric acid and borate were substituted for the buffering system of the invention. The resultant cream raised concerns about boron toxicity, such that it would be unacceptable for use on infants based on current medical knowledge.

EXAMPLE 3—CONTROL

The ingredients of Table 1 were combined, except that the naturally derived non-ionic, water soluble polymer was omitted. The resultant cream did not exhibit the proper viscosity. Additionally, increasing the concentration of stearic acid to obtain an acceptable viscosity resulted in the stearic acid having to be increased more than two-fold. Even then, the resultant cream did not possess the desirable properties of the cream associated with the invention.

EXAMPLE 4—CONTROL

The ingredients of Table 1 were combined, except that stearic acid was omitted. Without the inclusion of stearic acid, the desired viscosity was not able to be obtained regardless of how much naturally derived, non-ionic, water soluble polymer, preferably nonoxynyl hydroxyethylcellulose, was added.

EXAMPLE 5—INVENTION

The ingredients of Table 1 were combined as shown in Table 1. The resultant cream exhibited a pH of between 5 and 5.5, typically 5.2. Tests conducted with a Brookfield viscometer at spindle 4, 3 rpm, for two minutes disclosed a viscosity of 200,000 centipoise. The resultant diaper rash cream was acceptable for use on human skin. Under typical room temperature conditions the cream of this invention is a thick, viscous cream which is non-pourable.

EXAMPLE 6—CONTROL

The ingredients in Table 3 were combined, except that neither sodium citrate nor citric acid were added. The resultant lotion is easy to apply and remove, however, when subjected to extremes in pH, tends to become more ammoniacal if a base is added, but if a strong acid is added then it tends to become very acidic.

EXAMPLE 7—CONTROL

The ingredients of Table 3 were combined, except that boric acid and borate were substituted for the buffering system of the invention. The resultant lotion raised concerns about boron toxicity, such that it would be unacceptable for use on infants based on current medical knowledge.

EXAMPLE 8—BUFFERING CAPACITY OF INVENTION

To establish the efficacy of the buffering system of this invention, several experiments were conducted. In the first two experiments a 300 ml. aqueous solution of 3% sodium citrate and 0.5% citric acid was prepared. In the first experiment, the results of which are set forth in Table 5, a 0.036% aqueous solution of HCl was prepared and titrated into the buffer solution with agitation. In the second experiment, the results of which are set forth in Table 6, a 0.06% aqueous solution of NH3 was prepared and titrated into the buffer solution with agitation. In both cases, the pH was measured at frequent intervals.

TABLE 5

| BUFFERING IN PRESENCE OF ACID | |
| --- | --- |
| GRAMS OF HCl SOLUTION ADDED | pH |
| 0 | 5.49 |
| 4.4 | 5.42 |
| 9.6 | 5.41 |
| 14.3 | 5.40 |
| 19.5 | 5.39 |
| 24.7 | 5.38 |
| 32.4 | 5.37 |
| 38.8 | 5.38 |
| 43.8 | 5.37 |
| 49.3 | 5.37 |
| 55.4 | 5.35 |
| 63.6 | 5.35 |
| 67.3 | 5.35 |

TABLE 6

| BUFFERING IN PRESENCE OF BASE | |
| --- | --- |
| GRAMS OF NH3 SOLUTION ADDED | pH |
| 0 | 5.50 |
| 5.1 | 5.44 |
| 10.2 | 5.44 |
| 15.3 | 5.43 |
| 23.0 | 5.44 |
| 30.0 | 5.44 |
| 38.6 | 5.45 |
| 49.6 | 5.47 |
| 61.0 | 5.47 |

TABLE 6-continued

| BUFFERING IN PRESENCE OF BASE | |
| --- | --- |
| GRAMS OF NH3 SOLUTION ADDED | pH |
| 77.0 | 5.49 |

In the third experiment, 15 grams of the cream of the formulation of Table 1 were placed in a beaker. Measured amounts of a 0.06% aqueous solution of NH3 were added and mixed with the cream for two minutes. The pH was measured at three time intervals after the mixing. The results are set forth below in Table 7.

TABLE 7

| BUFFERING OF INVENTION | | | |
| --- | --- | --- | --- |
| Grams of NH3 Solution Added | pH after 5 minutes | pH after 30 minutes | pH after 3 Hours |
| 8 | 5.39 | 5.32 | 5.27 |
| 12 | 5.63 | 5.51 | 5.35 |
| 16 | 6.08 | 5.71 | 5.35 |
| NH3 Solution Control | 10.49 | 10.48 | 10.09 |

The results of these three experiments show that the diaper rash cream of this invention is extremely effective in buffering the effects of acidic feces or alkaline urine.

EXAMPLE 9—ABSORPTION TESTS

The diaper rash cream embodiment of this invention having the formulation of Table 1, as well as modified compositions having 5%, 10%, and 30% Dimethicone concentrations, was compared with Desitin which is a leading diaper rash ointment having zinc oxide as its protectant. (Desitin is distributed by the Consumer Health Care Division of Pfizer, Inc. of New York, N.Y., U.S.A.) In this test, for each sample tested, the first step was to weigh a clean, glass microscope slide ("original slide weight"). A coating of the sample to be tested was uniformly applied to one half of one side of the clean slide. The coated slide was then weighed ("original coated slide weight"). The coated slide then had its coated portion immersed in 100 ml. of purified water. The beaker with the partially immersed slide was then placed in a 400 C. oven for 1 hour. After that time the slide was removed from the water and had its uncoated portions dried. The dried slide was then weighed, left at room temperature for 2 hours, and then weighed again ("final slide weight"). All samples were tested twice.

Percentage of absorption was determined by the following equation:

$$\% \text{ Absorption} = 100 \times \frac{\text{Final slide weight} - \text{original slide weight}}{\text{Original coated slide weight} - \text{original slide weight}}$$

The percentage of absorption indicates how much of the cream or ointment was removed by the water where "% absorption" is less than 100, or how much water was able to be absorbed as a percentage of the cream's weight where "% absorption" is greater than 100. In those cases, for example, a "% absorption" determination of 200 would mean that the cream was able to absorb its own weight in water, or in effect to double its weight due to apparent absorption.

As set forth below in Table 8, it will be noted that over time, while relatively little change occurred with respect to the weight of the ointment layer (in fact it lost some weight), the cream of this invention unexpectedly apparently absorbed the liquid into the creamas shown by the increase in weight.

TABLE 8

ABSORPTION of LIQUID

| Formulations Tested | % Absorption | |
|---|---|---|
| | First Trial | Second Trial |
| Diaper rash cream of this Invention - Table 1 | 216 | 214 |
| Modified Table 1 cream - 5% Dimethicone | 187 | 173 |
| Modified Table 1 cream - 10% Dimethicone | 186 | 198 |
| Modified Table 1 cream - 30% Dimethicone | 163 | 183 |
| Leading Zinc Oxide ointment | 98 | 98 |

The results from this experiment demonstrate a further unique aspect of the cream embodiment of this invention. Not only does the diaper rash cream of this invention counteract attempted dramatic shifts in pH due to its buffering capacity, but it also absorbs liquid into itself thereby minimizing the presence of alkaline or acidic solutions in actual contact with the skin.

The diaper rash cream and lotion of this invention are effective in preventing diaper rash. They are also easy to use, such that either my be washed off with soap and water. Also both are aromatically and tactilely pleasing.

Additionally a variety of delivery systems may be used. For example, with respect to the cream, it may be applied directly to the skin, either by hand or via wipes. With respect to the lotion, it may be applied directly to the skin by a variety of methods, or it may be applied through incorporating it into a wipe, or it may be applied through incorporating it into a diaper. If direct application is chosen, then it could be by means of applying the lotion to one's hand or hands and then rubbing the lotion onto the baby's skin, or it could be by spraying the lotion in a spray or stream from a spray pump or aerosol onto the baby's skin, or it could be by means of a roll-on or a dabbing device both of which are well known in the consumer products field.

In an embodiment of the invention comprising a wipe, a porous sheet is impregnated with the skin lotion which has been described herein. Such porous sheets are taught, for example in U.S. Pat. No. 4,904,524. In an embodiment of the invention comprising a diaper, at least the portion of the diaper which will contact the wearer's genitals and buttocks is impregnated with the skin lotion which has been described herein.

The cream preferably appears whitish in its dispenser, but rubs on clear and transparent. Similarly, the lotion preferably initially appears opaque and somewhat milky, but goes on to become clear and transparent. The viscosity of the lotion will vary dependent on the concentration of Dimethicone used and the presence or absence of sodium EDTA in the composition. When a low viscosity lotion is required, sodium EDTA in the range of about 0.01 to 1% by weight and a low concentration of Dimethicone in the range of about 1 to 15% by weight will be used in the formulation of the composition. When a more viscous lotion is desired, the composition will contain a relatively high concentration of Dimethicone in the range of about 15 to 30% by weight and also will contain no sodium EDTA.

While the diaper rash cream and lotion herein described constitute preferred embodiments of this invention, it is to be understood that the invention is not limited to either precise formulation and that changes may be made therein without departing from the scope of the invention which is defined in the appended claims.

We claim:

1. A skin lotion having viscosity of about 10 to 20,000 centipoise and a pH of about 3.5 to 6.5, said lotion comprising:
   (a) a linear polydimethylsiloxane polymer in a concentration by weight of about 1 to 30%;
   (b) a non-ionic emulsifier in a concentration by weight of about 1 to 10%, selected from the group consisting of polyoxyethylene sorbitan fatty acid esters, sorbitan fatty acid esters, polyoxyethylene alcohols, and polyoxyethylene fatty ethers;
   (c) sodium citrate in a concentration by weight of about 1 to 10%;
   (d) citric acid in a concentration by weight of about 0.17 to 1.7%;
   (e) a blend of propylene glycol, diazolidinyl urea, methyl paraben, and propyl paraben in a concentration by weight of about 0.2 to 3%;
   (f) disodium ethylene diamine tetraacetic acid in a concentration by weight not greater than about 1%;
   (g) water in a concentration by weight of about 50 to 95%; and
   (h) polypropylene glycol myristyl ether propionate in a concentration of not greater than about 5% by weight.

2. A skin lotion according to claim 1 wherein said sodium citrate and said citric acid cooperate to form a buffering system having a pH in the range of between about 3.5 and 6.5.

3. A skin lotion according to claim 2 wherein said sodium citrate and said citric acid cooperate to form a buffering system having a pH in the range of between about 4.5 and 6.0.

4. A skin lotion according to claim 2 wherein said sodium citrate and said citric acid cooperate to form a buffering system having a pH of about 5.0 and 5.5.

5. A skin lotion according to claim 1 wherein said skin lotion has a neutral olfactory sensation.

6. A skin lotion according to claim 1 wherein said skin lotion is soluble in soap and water, said sodium citrate and said citric acid cooperating to form a buffering system having a pH in the range of between 3.5 and 6.5.

7. A skin lotion according to claim 1 which includes aloe vera in concentration by weight of about 0 to 5%.

8. A skin lotion according to claim 1 wherein said lotion is delivered to skin by means of a wipe, a diaper, a spray from an aerosol or pump dispenser, a roll-on or a dabber.

9. A skin lotion according to claim 1 having a viscosity of about 10 to 500 centipoise and a pH of about 4.5 to 6.0, wherein said linear polydimethylsiloxane polymer is of a concentration of about 5 to 20% by weight, said emulsifier is of a concentration of about 2 to 6% by weight, said sodium citrate is of a concentration of about 1 to 8% by weight, said citric acid is of a concentration of about 0.1 to 1.3% by weight, said water is of a concentration of about 60 to 90% by weight, said sodium ethylenediamine tetraacetic acid is of a concentration of about 0 to 0.5% by weight, and said blend of propylene glycol, diazolidinyl urea, methyl paraben, and propyl paraben is of a concentration of about 0.2 to 2% by weight.

10. A skin lotion according to claim 1 having a viscosity of about 10 to 100 centipoise and a pH of about 5.0 to 5.5, wherein said linear polydimethylsiloxane polymer is of a concentration of about 8 to 12% by weight, said emulsifier is of a concentration of about 3 to 5% by weight, said sodium citrate is of a concentration of about 2 to 5% by weight, said citric acid is of a concentration of about 0.33 to 0.83% by weight, said water is of a concentration of about 70 to 85% by weight, said sodium ethylenediamine tetraacetic acid is of a concentration of about 0 to 0.3% by weight, and said blend of propylene glycol, diazolidinyl urea, methyl paraben, and propyl paraben is of a concentration of about 0.5 to 1.5% by weight.

11. A skin lotion according to claim 1 having a viscosity of about 1,000 to 20,000 centipoise and a pH of about 3.5 to 6.5, wherein said linear polydimethylsiloxane polymer is of a concentration of about 15 to 30% by weight, said emulsifier is of a concentration of about 1 to 10% by weight, said sodium citrate is of a concentration of about 1 to 10% by weight, said citric acid is of a concentration of about 0.1 to 1.7% by weight, said water is of a concentration of about 60 to 90% by weight, said sodium ethylenediamine tetraacetic acid is of a concentration of about 0 to 0.1% by weight, and said blend of propylene glycol, diazolidinyl urea, methyl paraben, and propyl paraben is of a concentration of about 0.2 to 3% by weight.

12. A skin lotion according to claim 1 having a viscosity of about 8,000 to 18,000 centipoise and a pH of about 4.5 to 6.0, wherein said linear polydimethylsiloxane polymer is of a concentration of about 15 to 30% by weight, said emulsifier is of a concentration of about 2 to 6% by weight, said sodium citrate is of a concentration of about 1 to 8% by weight, said citric acid is of a concentration of about 0.1 to 1.3% by weight, said water is of a concentration of about 60 to 90% by weight, said sodium ethylenediamine tetraacetic acid is of a concentration of about 0 to 0.1% by weight, and said blend of propylene glycol, diazolidinyl urea, methyl paraben, and propyl paraben is of a concentration of about 0.2 to 2% by weight.

13. A skin lotion according to claim 1 having a viscosity of about 10,000 to 15,000 centipoise and a pH of about 5.0 to 5.5, wherein said linear polydimethylsiloxane polymer is of a concentration of about 18 to 22% by weight, said emulsifier is of a concentration of about 3 to 5% by weight, said sodium citrate is of a concentration of about 2 to 5% by weight, said citric acid is of a concentration of about 0.3 to 0.9% by weight, said water is of a concentration of about 70 to 90% by weight, said sodium ethylenediamine tetraacetic acid is of a concentration of about 0 to 0.1% by weight, and said blend of propylene glycol, diazolidinyl urea, methyl paraben, and propyl paraben is of a concentration of about 0.5 to 1.5% by weight.

* * * * *